(12) United States Patent
Kanzaki et al.

(10) Patent No.: US 7,733,476 B2
(45) Date of Patent: Jun. 8, 2010

(54) DEFECT INSPECTION APPARATUS AND METHOD

(75) Inventors: Toyoki Kanzaki, Kyoto (JP); Tatsuo Ohka, Kyoto (JP); Teruhiko Ikeda, Kyoto (JP)

(73) Assignee: Horiba, Ltd., Kyoto (JP)

( * ) Notice: Subject to any disclaimer, the term of this patent is extended or adjusted under 35 U.S.C. 154(b) by 95 days.

(21) Appl. No.: 11/965,507

(22) Filed: Dec. 27, 2007

(65) Prior Publication Data

US 2008/0158560 A1 Jul. 3, 2008

(30) Foreign Application Priority Data

Dec. 28, 2006 (JP) .......................... P2006-355908

(51) Int. Cl.
*G01N 21/00* (2006.01)
(52) U.S. Cl. ................................. 356/237.4; 356/237.5
(58) Field of Classification Search .... 356/237.1–237.5
See application file for complete search history.

(56) References Cited

U.S. PATENT DOCUMENTS

| 4,610,541 | A | * | 9/1986 | Tanimoto et al. | 356/239.8 |
| 4,669,875 | A | * | 6/1987 | Shiba et al. | 356/237.3 |
| 4,676,637 | A | * | 6/1987 | Uto et al. | 356/237.4 |
| 4,795,911 | A | * | 1/1989 | Kohno et al. | 250/559.18 |
| 5,017,798 | A | * | 5/1991 | Murakami et al. | 250/559.06 |
| 5,359,407 | A | * | 10/1994 | Suzuki et al. | 356/237.2 |
| 5,528,360 | A | * | 6/1996 | Kohno | 356/237.5 |
| 5,717,198 | A | * | 2/1998 | Broude et al. | 250/205 |
| 5,963,316 | A | * | 10/1999 | Miura et al. | 356/237.3 |
| 6,292,259 | B1 | * | 9/2001 | Fossey et al. | 356/237.2 |

FOREIGN PATENT DOCUMENTS

| JP | 59-082726 | 5/1984 |
| JP | 62-046239 | 2/1987 |
| JP | 06-138046 | 5/1994 |
| JP | 07-229844 | 8/1995 |
| JP | 07-333827 | 12/1995 |
| JP | 10-163284 | 6/1998 |
| JP | 11-237226 | 8/1999 |
| JP | 2000-146850 | 5/2000 |
| JP | 2000-214099 | 8/2000 |
| JP | 2004-258384 | 9/2004 |

\* cited by examiner

*Primary Examiner*—Hoa Q Pham (57) ABSTRACT

The defect inspection apparatus and method for determining an acceptable condition of a reticle/mask member with a pattern area to be developed on a semiconductor device includes determining a non-pattern area and designating an inspection target area within a non-pattern area. Light is scanned across the inspection target area and detected to provide representative signals. The representative signals are processed to define the status of foreign matter including size and location and further compared with predetermined values to determine the acceptability of the mask for continued production purposes.

10 Claims, 8 Drawing Sheets

DEFECT INSPECTION APPARATUS AND METHOD

BACKGROUND OF THE INVENTION

1. Field of the Invention

The present invention relates to a defect inspection apparatus and method using the principle of scattered light capable of suitably inspecting any haze deposited on a reticle/mask or pellicle film and more particularly to selection of an inspection area and processing of detected results.

2. Description of Related Art

Conventionally, if a pattern area or pellicle film that forms a pattern of a reticle/mask used for exposure during manufacturing of, for example, a semiconductor device, has defects, such as an adhesion of foreign matters or a haze (foreign matter vapor-deposited or crystallized), the resultant manufactured semiconductor device can suffer a lowering of the production yield. Consequently, the pattern area of the reticle/mask and the pellicle film are inspected for defects by using a defect inspection apparatus.

In recent years, since the wavelength of light emitted by an exposure machine of a stepper has become shorter, the photochemical reaction has become stronger, so that even a small amount of a gas component in the environment, such as air, tends to become as a haze on the production product. Consequently, success or failure of haze detection largely affects the yield of a semiconductor device.

Accordingly, Japanese Unexamined Patent Publication No. 1995-229844 is an example of haze inspection by visually inspecting the entire surface of a reticle/mask or pellicle film with a microscope for haze inspection to provide a pattern defect apparatus with an improved S/N ratio and thereby with high sensitivity.

However, there is still a need to provide an economically improved defect inspection apparatus to address the specific characteristics of a reticle/mask.

SUMMARY OF THE INVENTION

However, in a conventional configuration, especially in the former haze inspection apparatus, since a haze in a developmental stage has a very small particle size, if it is not inspected with high sensitivity, the haze cannot be initially detected. Moreover, elaborate circuit patterns are being fabricated into microstructures in recent years, and consequently an effect of scattered light from the pattern has grown, therefore, there are increased problems of erroneous detection where although a haze is generated, it is determined that there is no haze and although no haze is generated, it can be determined that there is a haze.

In the latter haze inspection, an improved sensitivity comes with a lowering in the production throughput, and conventional apparatus are comparatively expensive. Therefore, it has a problem that using such conventional apparatus only for haze inspection is not good in efficiency.

The present invention is made to resolve such problems, and its primary object is to provide an excellent defect inspection apparatus that especially does not need to improve sensitivity, can detect suitably a haze of a small particle size, for example a haze in the developmental stage, in a relatively short time period, and is free from an erroneous detection by the effect of the scattered light from the circuit pattern.

That is, a defect inspection apparatus according to the present invention uses a light source for illuminating inspection light on an inspection target plane that has a pattern area in which a pattern is formed and a non-pattern area in which a pattern is not formed, a frame member for supporting a protective coat for preventing the adhesion of foreign matters, etc. in the pattern area and also being provided in a non-pattern area; a light scanning part for scanning the inspection light on the inspection target plane; and a photodetector for detecting light diffracted and/or scattered by the inspection target plane as detection light when the light scanning part scans the inspection light on the inspection target plane; wherein the inspection target area is intentionally set in the non-pattern area.

Here, specifying a configuration where "the inspection target area is set in the non-pattern area" results from research of the current inventors that found the following facts concerning development of a haze and its particular distribution mode. Note, here the non-pattern area being set for the inspection target area is a broad concept including not only an area that excludes the whole pattern area but an area that may exclude only a part thereof. That is, the inspection target area only needs to be an area of the pattern area from which an erroneously detectable area or an area with such a possibility is excluded from the inspection results.

Figure 1:
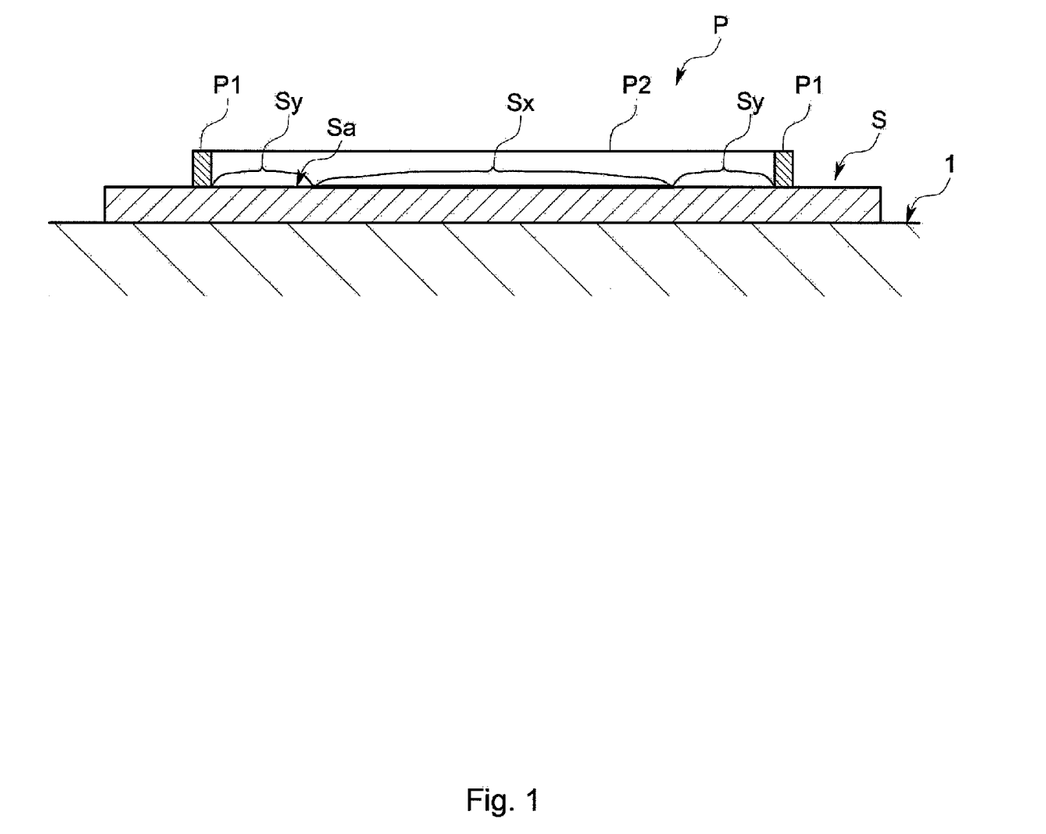
FIG. 1 is a diagram showing a state where a sample and a pellicle to be inspected by a defect inspection apparatus are mounted on a stage.

That is, consider a case where the reticle/mask S that is an inspection target forms a pattern area Sx of a substantially rectangular configuration, in a plan view, in substantially a center of, for example, a transparent glass substrate, as shown in FIG. 1 and has a pellicle substantially including a pellicle frame P1 substantially in the form of a rectangle that is installed in a standing manner so as to enclose outwardly positions being off-set from respective peripheries of the pattern area Sx and a pellicle film P2 being provided in a tensioned state between the upper end rims of this pellicle frame P1.

The inventors have discovered the following.

(1) First, a haze is generated in a non-pattern area Sy of the substrate that is in a neighborhood of the pellicle frame P1, and it develops toward the pattern area Sx. That is, there is a tendency for the haze to develop from the outside position to the inside of the area bounded by the pellicle frame P1.

(2) There is also a case, in the neighborhood of the pellicle frame P1, where hazes ranging from a comparatively large haze to a small haze are distributed and a small haze is frequently distributed in the neighborhood of the respective peripheries of the pattern area Sx.

The inventors adopted this observed model configuration because of the following observations. Accordingly, when inspection of a haze in the non-pattern area is performed, if there is no generation of a haze in the non-pattern area, it can be determined that a haze is also not generated in the pattern area. In addition, in a stage when it is determined that a haze exists in the non-pattern area or is generated in a manner approaching a predetermined area in the pattern area, if a prophylactic measure, such as a cleaning or an exchange of the pellicle/mask or even halting its continued use, is taken, lowering of the production yield of the semiconductor device by the occurrence of haze can be prevented.

If the inspection target area is also set in the non-pattern area and haze inspection is performed in this non-pattern area, the problem of erroneous detection by the effect of the scattered light from the pattern will be lessened. In addition, since in a case where the sensitivity is improved in order to inspect a haze whose particle size is small, for example, a haze in a developmental stage, only the non-pattern area needs to be inspected and the inspection time period becomes short compared with a case of inspecting the entire surface like the conventional case.

Besides, only by obtaining an inspection result where there is no haze in the non-pattern area, can it be determined that there is no development of a haze also in the pattern area, and a shortening of the inspection time can be attained. Furthermore, when it is determined that a haze exists or is growing in the non-pattern area, if a measure, such as cleaning or exchange of the pellicle/mask or at least a halting of its use is taken at that stage, it becomes possible to prevent the production yield of the semiconductor device from being lowered by the haze.

The present invention can provide an excellent defect inspection apparatus and method that, although being relatively simple in implementation, can still detect a haze with high precision and at high speed and thereby prevent the yield of the semiconductor device from being lowered by the haze.

As one desired mode of the present invention, an embodiment can include a haze size calculation part for calculating a particle size of a haze based on detection light detected by a photodetector when the inspection target area is scanned, and a particle size variation determination part for determining whether the particle size of the haze obtained by the haze size calculation part has become larger by a comparison with the inspection result of a preceding measurement of the same target area, the previous measurements being stored for comparison purposes.

For example, in a case where the particle size of the haze obtained by the haze size calculation part has become larger than the particle size of the haze of the last inspection result, it is considered that the haze is growing. Therefore, when the particle size variation determination part outputs a determination result that the particle size of the haze obtained by the haze size calculation part has become larger than the particle size of the haze of the last inspection result, it is possible to take a preventative measure of cleaning or exchange of the reticle/mask or the pellicle that is the inspection target or halt its use, and consequently it becomes possible to prevent the production yield of the semiconductor device from being lowered by the haze.

Moreover, if the defect inspection apparatus has a clearance calculation part for calculating a clearance measurement from a haze to the pattern area based on the detection light that is detected by the photodetector when the inspection target area is scanned, and if it is considered that the clearance has become shorter by, for example, recording a clearance at each inspection and comparing it with its stored history, it can be concluded that the haze is growing and can be monitored to project a corrective action.

Further, in the case where the apparatus has a clearance determination part for determining whether the clearance from the haze to the pattern area obtained by the clearance calculation part is equal to or less than a predetermined distance, and if the clearance determination part outputs a determination result that the clearance from the haze to the pattern area obtained by the clearance calculation part is equal to or less than the predetermined distance, it is possible to take the same preventative measure as the above-mentioned measures and consequently it becomes possible to prevent the production yield of the semiconductor device from being lowered by the haze problem.

Incidentally, there can be a case where the haze grows from an initial state in which comparatively small hazes are distributed only at positions distant from the pattern area, and the hazes are not initially distributed at positions near the pattern area and the haze distribution, after subsequent growth becomes such that comparatively large hazes are distributed at positions distant from the pattern area while smaller hazes are distributed at positions near the pattern area and acceptable yields of semi-conductor devices can be maintained.

Therefore, the detection inspection apparatus can be configured to have a haze distribution calculation part for calculating a distribution of the haze based on the detection light detected by the photodetector when the inspection target area is scanned and a haze distribution output part for outputting the haze distribution obtained by the haze distribution calculation part, and when a subsequent haze distribution outputted by the haze distribution output part is one that shows an increased haze distribution after growth, it is considered that the haze is growing. Also in such a case, the same measure as the above mentioned can be taken, and if doing so, it becomes possible to prevent the yield of the semiconductor device from being lowered by the haze.

As a further desirable mode of this invention, there can be given an embodiment that has a haze distribution calculation part for calculating a distribution of the haze in the non-pattern area based on the detection light detected by the photodetector when the inspection target area is scanned and a distribution state determination part for determining whether the haze distribution obtained by the haze distribution calculation part shows a predetermined distribution state.

Here, when the predetermined distribution state, for example, if a "state in which comparatively large hazes are distributed at positions distant from the pattern area, and smaller hazes are distributed at positions near the pattern area" is stored, the apparatus can take the above-mentioned measure based on a comparison result with this predetermined distribution state.

According to the defect inspection apparatus and method of the present invention, the inspection target area is set in the non-pattern area and when the non-pattern area is inspected, a problem of erroneous detection by the effect of the scattered light from the pattern is not generated. Further, in the case where the sensitivity of measurement is improved in order to inspect a haze whose particle size is small, for example, a haze in the developmental stage, what is necessary is to inspect only the non-pattern area; therefore, the inspection time period can be made short compared with a case of inspecting the entire surface of the reticle/mask in a conventional manner.

Moreover, by obtaining an inspection result that there is no haze in the non-pattern area, it can be determined that there is also no generation of a haze in the pattern area, and shortening of the inspection time period can be attained. Furthermore, when it is determined that a haze exists or is growing in the non-pattern area, if a measure, such as cleaning or exchange of the pellicle or halt of its use, is taken at that stage, it becomes possible to prevent the production yield of the semiconductor device from being lowered by the haze.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Hereafter, referring to the drawings, one embodiment of the present invention will be described.

Figure 2:
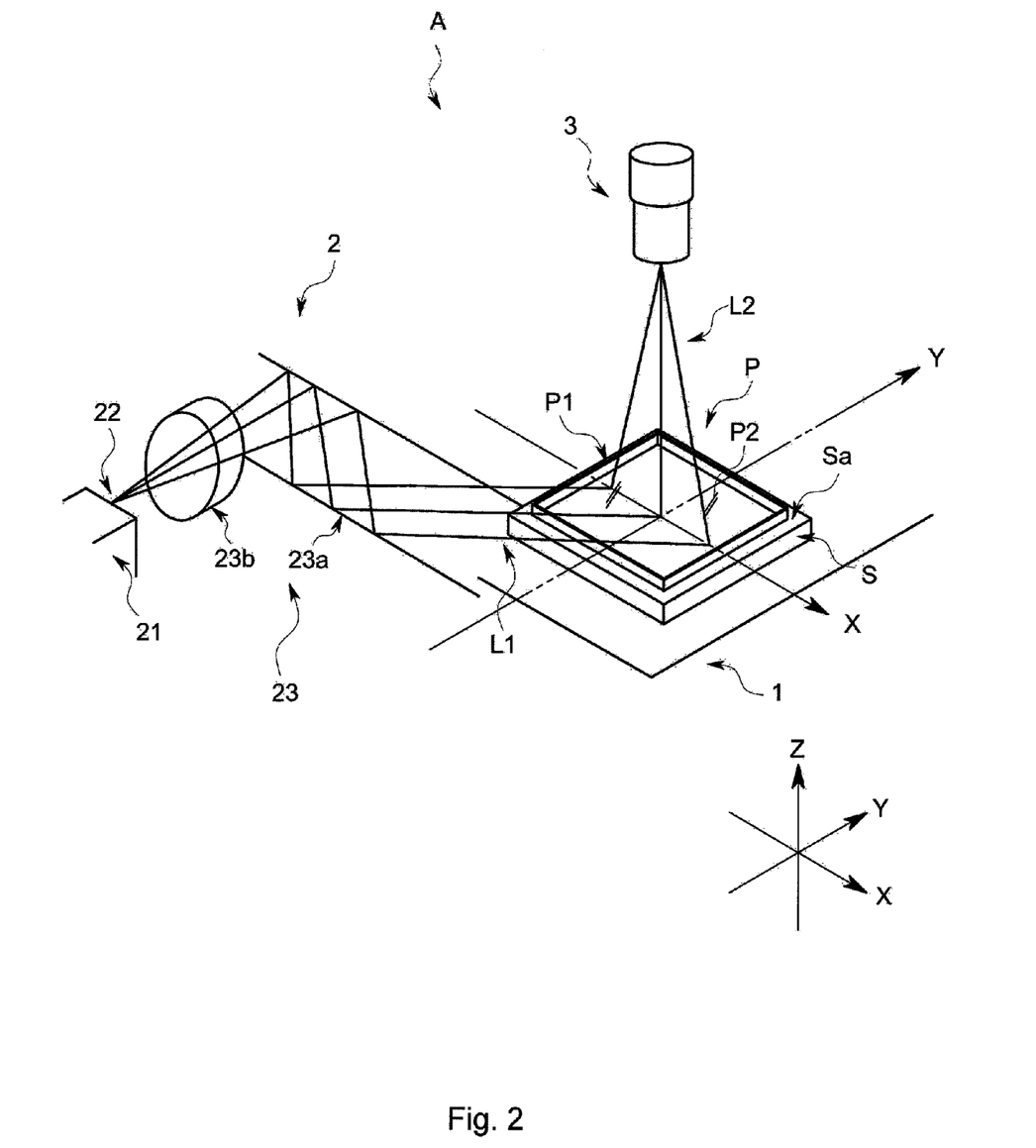
FIG. 2 is a general schematic diagram schematically showing a configuration of a defect inspection apparatus of the first embodiment.
Figure 3:
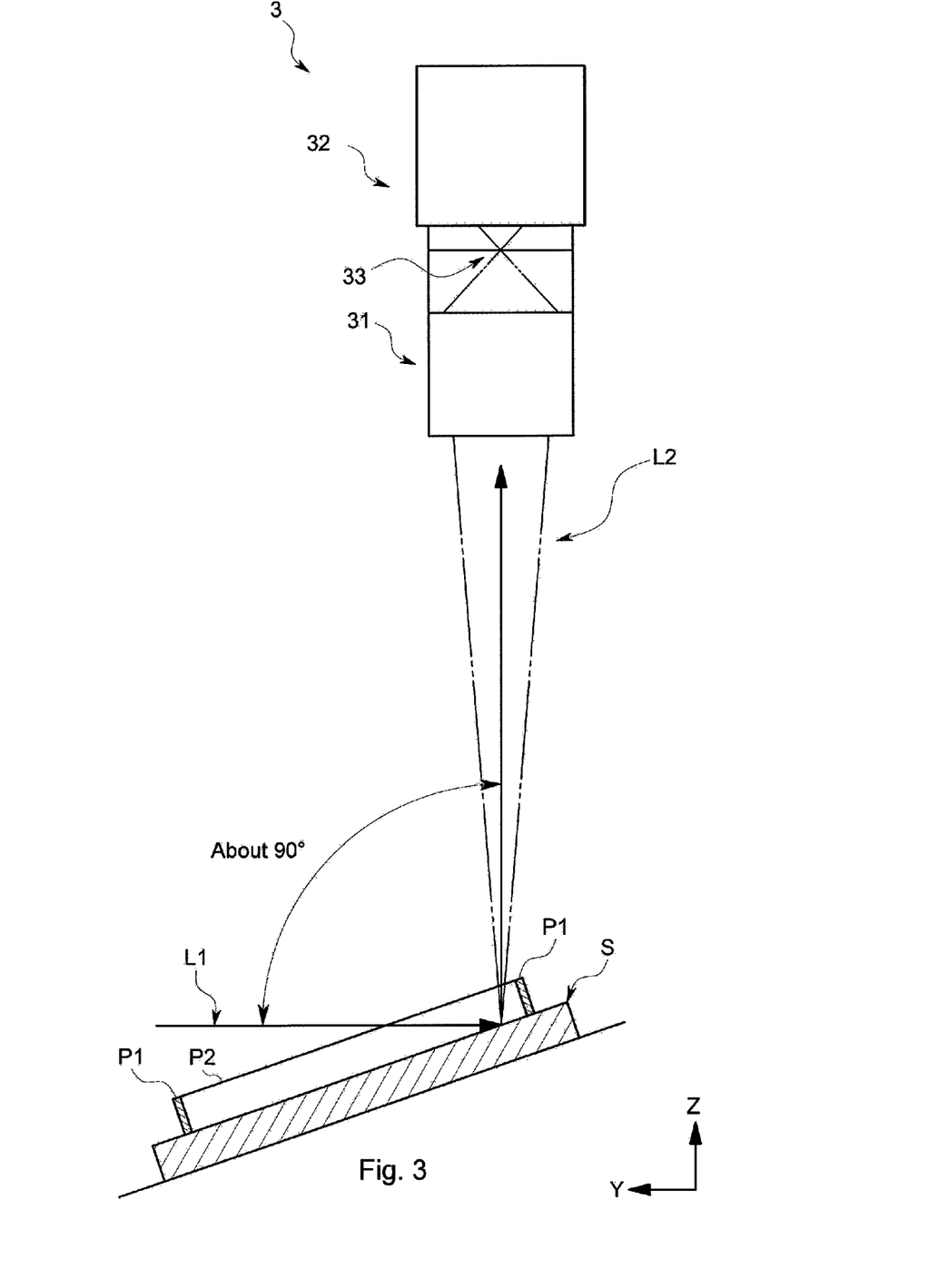
FIG. 3 is a diagram showing an arrangement relationship of a sample, and a light detection system, in the first embodiment.

A defect inspection apparatus A according to the present embodiment, as shown in FIG. 1 and FIG. 2, inspects a defect in a reticle/mask (hereinafter called a sample S) that is an inspection target and has a pattern area Sx in which an unillustrated pattern is formed and a non-pattern area Sy in which a pattern is not formed in its surface Sa. The surface Sa being covered with a pellicle film P2 that is a protective coat for preventing the adhesion, etc. of foreign matters, and, as shown in FIGS. 2 and 3, includes a stage 1 on which the sample S is mounted; a light illumination system 2 for illuminating inspection light L1 on the sample S mounted on this stage 1 wherein the inspection light L1 is scanned; a light detection system 3 for detecting light diffracted and/or scattered by the surface Sa and/or the pellicle film P2 of the sample S as detection light L2 when the light scanning system scans the inspection light L1 on the inspection target plane (the surface of the sample S or the surface of the pellicle film P2); and an information processor 4 for determining any generation of a haze, etc. Hereafter, each part will be explained in more detail.

The stage 1 can be movable along an X-axis, a Y-axis, and a Z-axis, and is configured to be able to inspect the entire surface, Sa, of the sample S when mounted on the stage 1 by moving in a direction perpendicular to a scanning direction of the inspection light L1 at a constant speed, in cooperation with scanning of the laser beam that is the later-described inspection light L1. In the present embodiment, the stage 1 is configured to output a stage address signal showing a stage address (X-coordinate, Y-coordinate, and Z-coordinate) to the information processor 4.

The light illumination system 2 has, as shown in FIG. 2, a laser light source 21 (for example, a He—Ne laser light source) for emitting a laser beam that is the inspection light L1, a beam expander 22 for appropriately expanding the inspection light L1 emitted from this laser light source 21, and a light scanning part 23 substantially including a scanning mirror 23a (for example, a galvano-mirror) for scanning the inspection light L1 which can be expanded by the beam expander 22 and bringing it into focus on the inspection target plane (the surface Sa or the pellicle film P2) and a scanning lens 23b (for example, an fθ lens).

In addition, in the present embodiment, the apparatus is so configured that the inspection light L1 may be calculated relative to the specific pattern of the sample to be incident on the surface Sa, for example, at angles of 10 to 40° (incident angle being 50 to 80°) and scans substantially the whole surface of Sa using the light scanning part 23. A mirror angle signal indicating a mirror angle of the scanning mirror 23a may be outputted to the information processor 4. The inspection position (defect position) on the surface Sa can be specified from this mirror angle signal (in this example, the X-coordinate) and the above-mentioned stage address signal (in this example, the Y-coordinate) to calculate the specific inspection area of the present invention on a periphery of the circuit pattern.

The light detection system 3, having an optical axis in a YZ plane of FIG. 3, is disposed between a position substantially perpendicular to the surface Sa and a position that makes an angle of less than the reflection angle equal to the incident angle, preferably a position at which a scattering angle to the inspection light L1 becomes 90°, and has a condensing lens system 31, a photodetector 32, and a slit 33 disposed between these condensing lens system 31 and photodetector 32. Here, the "scattering angle" means an angle directing to the optical axis of the photodetector 32 from the direction of propagation of probe light (inspection light L1) with a scattering object on the center.

"About 90°" in FIG. 3 is the supplementary angle thereof. Incidentally, this light detection system 3 may be arranged on the right-and-left both sides in the X-direction in a plane inclined to the sample surface Sa between the XY plane and the YZ plane.

The condensing lens system 31 can be made up of a single lens or a combination of a plurality of lenses, and is configured to make the detection light L2 focus on the photodetector 32. The type of lens and how to combine lenses may be appropriately selected according to particular conditions of a sample target.

The photodetector 32 converts information of the intensity, frequency, phase, etc. of the detected scattered light into electric signals and outputs this as a scattered-light detection signal to the information processor 4, for example, a PMT (Photo Multiplier Tube), a line sensor, or the like can be used. In a case where the photodetector 32 is the PMT, the slit 33 and a scanning line on the surface Sa are arranged so as to be optically conjugate to each other, as in FIG. 3. In a case where the photodetector 32 is the line sensor, the line sensor and the scanning line on the surface Sa are arranged so as to be optically conjugate to each other.

Moreover, in the present embodiment, the photodetector 32 is disposed in a direction perpendicular to a scanning line of the inspection light L1 and to be near the center of the scanning line (near the center of the surface Sa). The photodetector 32 also satisfies an optical arrangement in which an optical axis thereof is disposed between a position making a scattering angle of roughly 90° and a position vertical to the surface Sa, allowing the single photodetector 32 to see all of the scanning line.

The slit 33 can be in the form of an oblong shape and substantially rectangle with a slit penetrating in a thickness direction of a planar member. In the present embodiment, the slit 33 is provided immediately in front of a light incident side of the photodetector 32 with its longitudinal direction substantially in agreement with the scanning direction of the surface Sa, being constructed so that a part of the focused light by the condensing lens system 31 is led to the photodetector 32.

Figure 4:
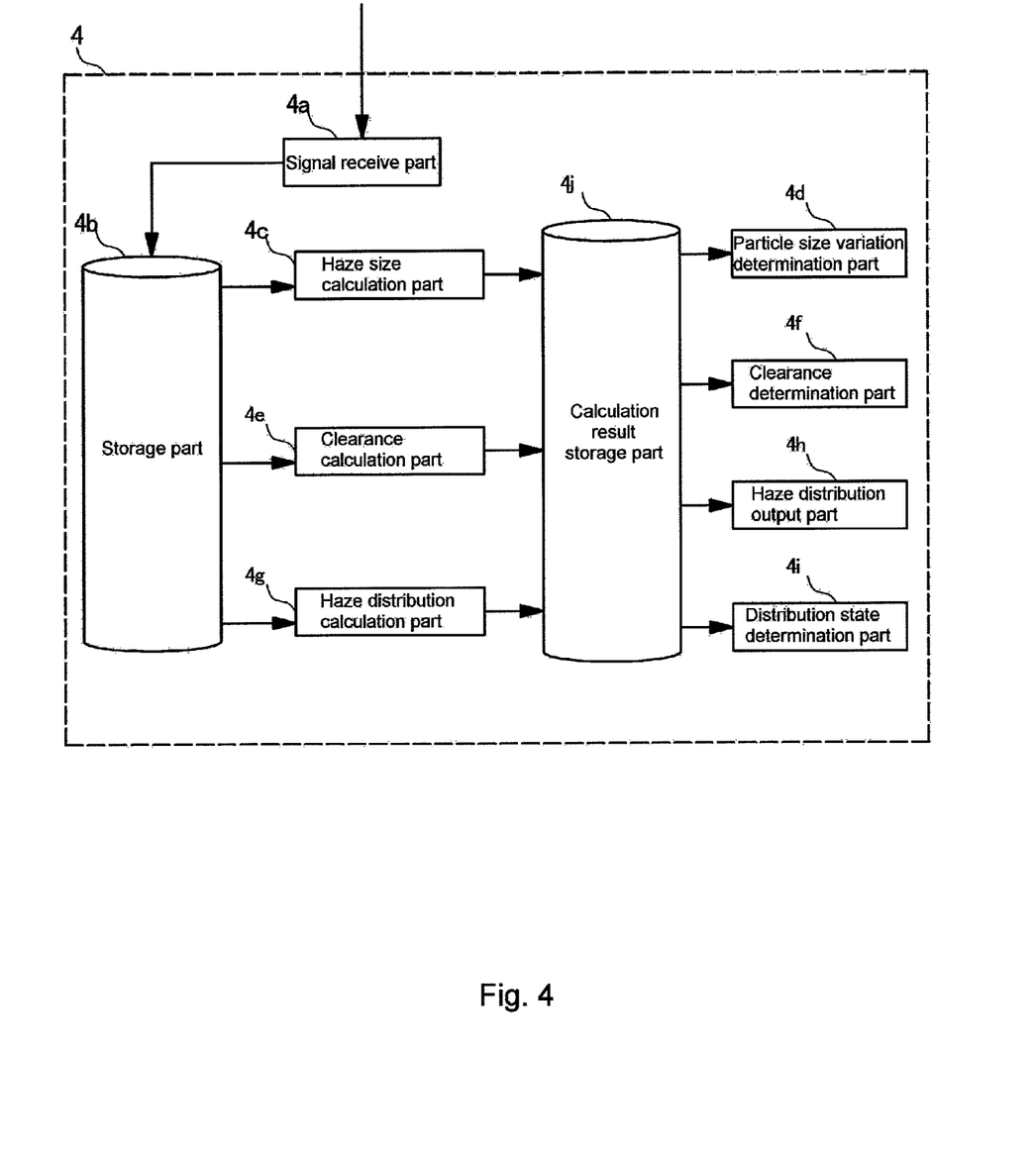
FIG. 4 is a function block diagram of an information processor in the first embodiment.

The information processor 4 is constructed with a digital and analog electric circuit having an unillustrated CPU, an internal memory, an A/D converter, a D/A converter, a communication interface for communicating with the stage 1, the scanning mirror 23a, an input interface, a display device of a liquid crystal display, and other supplemental devices. The information processor 4 may be of exclusive use or may be configured to use a general purpose computer, such as a personal computer, for a part or the whole thereof.

Moreover, the information processor 4 may be constructed with only analog circuits without a CPU so as to satisfy functions as the next respective parts. It is not necessary for the information processor 4 to be physically one body, thereby allowing for an external personal computer to serve it for a part of the functions or by other methods. The information processor 4 may be constructed with a plurality of devices mutually connected by wire or by radio wave.

The information processor 4 is configured to store a predetermined program in an internal memory, which can make the CPU and its peripheral devices work cooperatively according to the program, whereby this information processor 4 performs, as shown in FIG. 4, and at least functions as a signal receive part 4a, a storage part 4b, a haze size calculation part 4c, a particle size variation determination part 4d, a clearance calculation part 4e, a clearance determination part 4f, a haze distribution calculation part 4g, a haze distribution output part 4h, a distribution state determination part 4i, and a calculation result storage part 4j. Hereafter, each part will be explained in detail.

The signal receive part 4a receives the stage address signal outputted by the stage 1, the mirror angle signal outputted by the scanning mirror 23a, and the scattered-light detection signal outputted by the photodetector 32, respectively.

The storage part 4b stores an inspection position obtained from the stage address that the stage address signal received by the signal receive part 4a, and a mirror angle indicated by the mirror angle signal, and the intensity of light indicated by the scattered-light detection signal, with the two being associated with each other.

Figure 5:
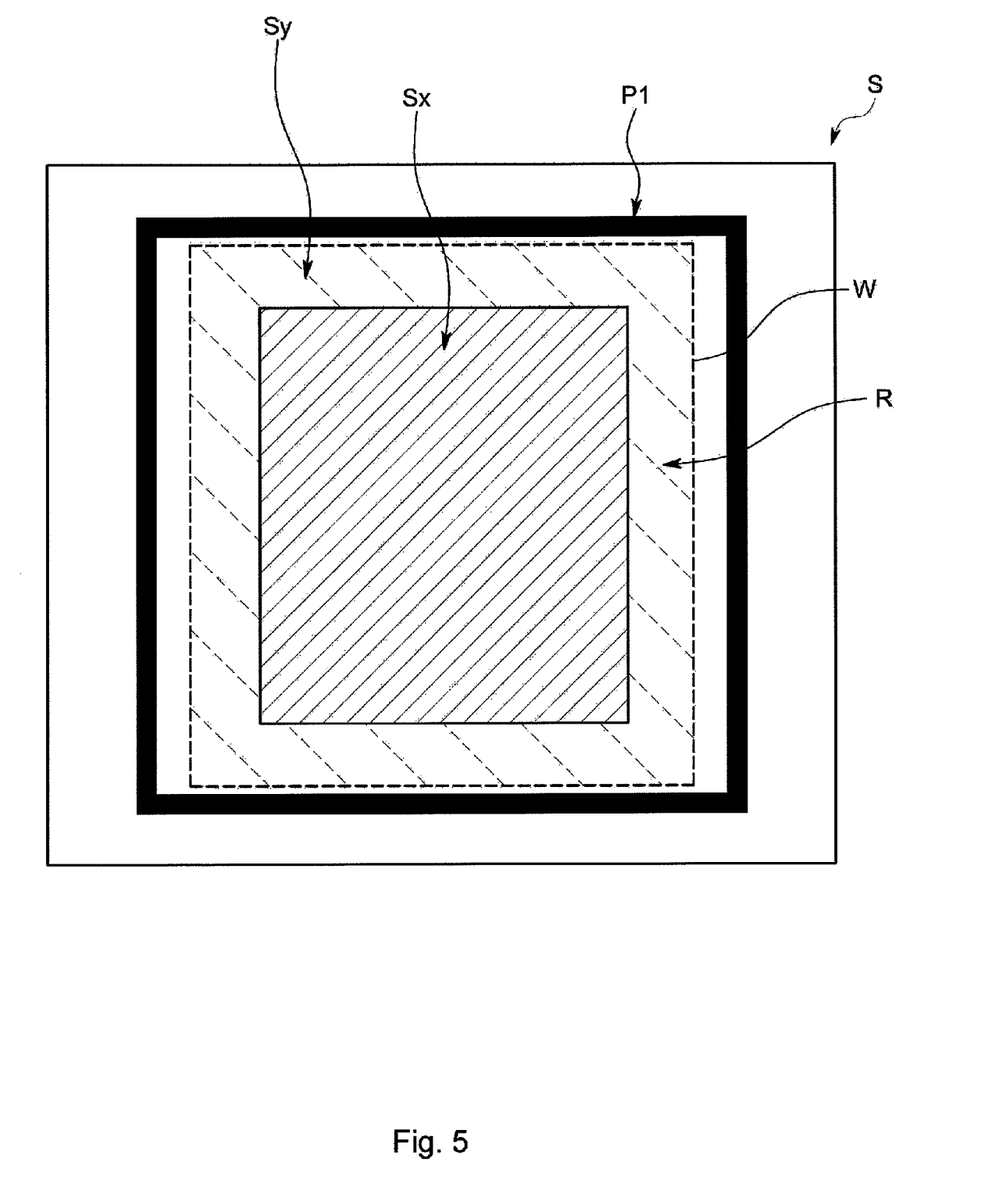
FIG. 5 is a schematic diagram for explaining the sample and an inspection target area of a pellicle in the embodiment (when there is no generation of a haze)

Here, in the present embodiment, the storage part 4b is configured to determine whether an inspection position at which the intensity of light indicated by the scattered-light detection signal exceeds a predetermined threshold in storing in the storage part 4b exists in an inspection target area R (portion hatched by dashed lines) sandwiched by a dashed line frame W obtained by connecting points provided at a predetermined distance from a pellicle frame (frame member) P1 as shown in FIG. 5 and the desired pattern area Sx. When it is determined that the inspection position is within the area, storage is performed in which the intensity of light and the inspection position are correlated with each other. Thus, inspection positions stored in the storage part 4b that would fall within the circuit pattern area Sx will be excluded and the inspection results will be directed to a non-pattern area in accordance with the theory of the present invention.

The haze size calculation part 4c calculates the particle size of haze based on the detection light L2 detected by the photodetector 32.

The haze size calculation part 4c is configured to calculate a particle size of each measured haze result when the non-pattern area Sy, that is the inspection target area, is scanned, based on the intensity of the scattered light stored in the storage part 4b. Then, it is configured to store the calculation result in a calculation result storage part 4j. As an alternative method, since the scattered light can be continuously detected from the haze of a large particle size by this operation, the particle size can be calculated based on an interval of the scattered-light detection signal.

The particle size variation determination part 4d determines whether the particle size of the haze obtained by the haze size calculation part 4c has become larger by a comparison with previous multiple time inspection results of the same particle size location of the haze.

The particle size variation determination part 4d determines that the haze is growing if the particle size of the haze existing at a predetermined inspection position at the time of the (n+1)-th inspection has become larger than the particle size of the haze at the time of the n-th inspection. Here, n is a natural number. For example, a particle size Ca2 (see FIG. 7) of the haze Ha being inspected at this time and a particle size Ca1 (see FIG. 6) of the haze Ha that existed substantially at the same position as a position of the last inspection time are compared. If the particle size Ca2 of the haze Ha of this time inspection is larger than the particle size Ca1 of the haze Ha of the last time inspection, it is determined that the haze Ha in question and other hazes are growing. Then, in the present embodiment, this particle size variation determination part 4d is configured to, when it determines that the particle size of the haze is growing, output that the haze is growing in a recognizable manner.

The clearance calculation part 4e calculates the clearance (hereinafter called an inspection clearance) from the haze to the pattern area Sx when the non-pattern area Sy, that is the inspection target area, is scanned based on the detection light L2 detected by the photodetector 32.

Figure 6:
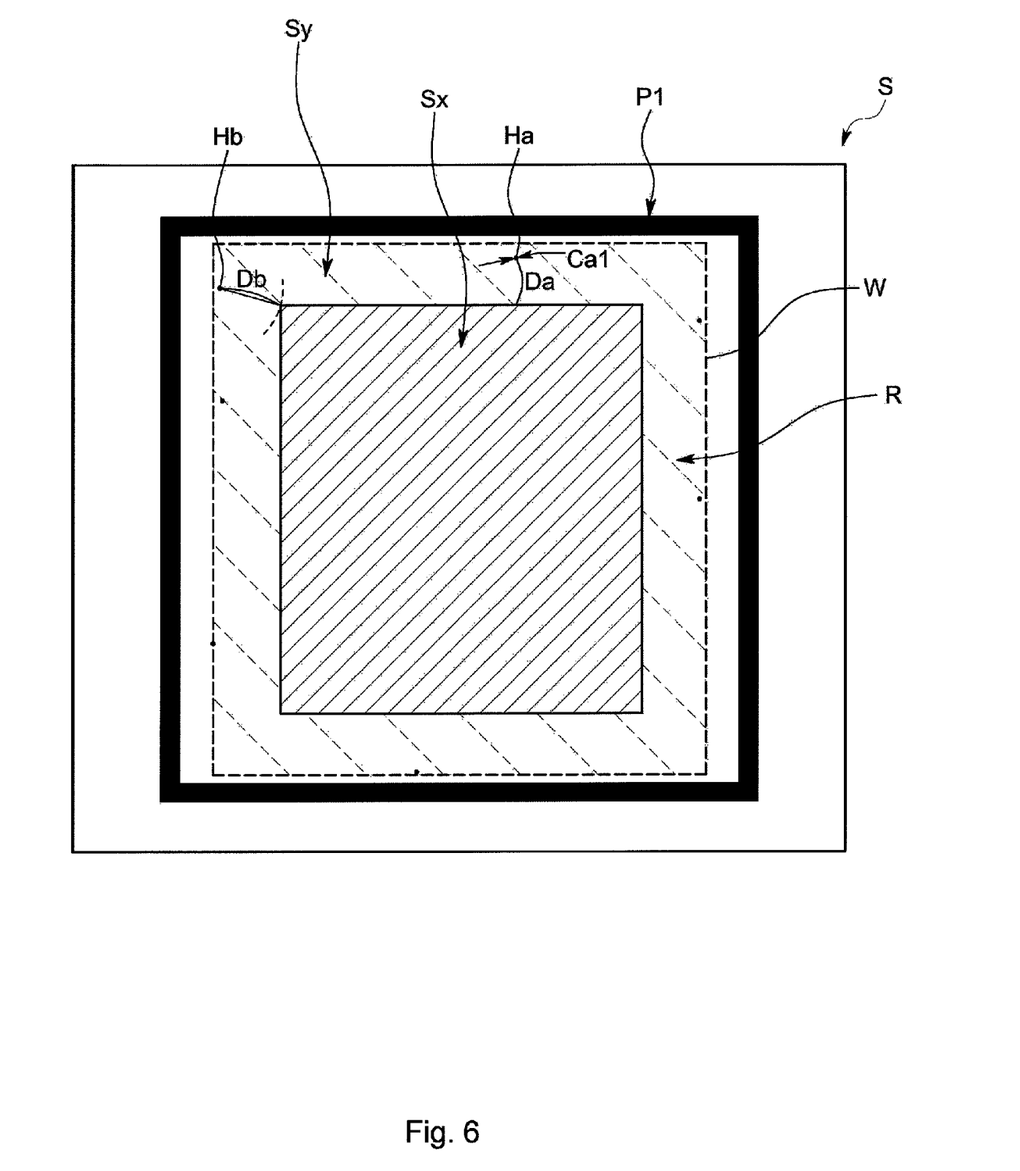
FIG. 6 is a diagram showing a state where a haze is generated in an initial stage.

The clearance calculation part 4e is configured to calculate the inspection clearance for each haze based on the inspection position value on the surface Sa obtained from the stage address signal and the mirror angle signal stored in the storage part 4b. For example, as shown in FIG. 6, for the haze Ha, the inspection clearance Da that is a minimum distance from the haze Ha to the pattern area Sx is found by calculation, for the haze Hb, the inspection clearance Db that is a minimum distance from the haze Hb to the pattern area Sx is also found by calculation. The clearance calculation part 4e is configured to make the calculation result storage part 4j store the calculation result.

Incidentally, although in the present embodiment, the haze that is targeted for calculation of the clearance is specified to be one whose particle size obtained by the haze size calculation part 4c is equal to or more than a predetermined size, it is also possible that what is targeted to obtain the inspection clearance may be all the hazes or can be hazes of arbitrary particle sizes.

The clearance determination part 4f determines whether the inspection clearance obtained by the clearance calculation part 4e is equal to or less than a stored predetermined distance.

The clearance determination part 4f determines whether the inspection clearance stored in the calculation result storage part 4j is equal to or less than the predetermined distance.

In the present embodiment, this clearance determination part 4f is configured to output a report that the haze is growing when it is determined that the inspection clearance stored in the calculation result storage part 4j was equal to or less than the predetermined distance.

The haze distribution calculation part 4g calculates a distribution of hazes in the non-pattern area Sy, that is the inspection target area, based on the detection light L2 detected by the photodetector 32 and an inspection position.

In the present embodiment, the haze distribution calculation part 4g first calculates a size of each haze being generated in the non-pattern area Sy that is the inspection target area in the same way as the haze size calculation part 4c, and calculates a haze distribution added with particle size information from the inspection position of each haze and a stage address position. Then, the haze distribution calculation part 4g is configured to store the calculation result in the calculation result storage part 4j. Incidentally, a haze that is considered as a target for which a haze distribution is found may be a haze whose particle size is equal to or more than the predetermined size, or all the hazes may be targeted, or a haze distribution may be obtained for haze with an arbitrary particle size. Moreover, for calculation of the haze distribution, a calculation result by the haze size calculation part 4c or by the clearance calculation part 4e can be allowed to be used.

The haze distribution output part 4h outputs the haze distribution obtained by the haze distribution calculation part 4g. The haze distribution output part 4h is configured to perform an outputting of the haze distribution on a display screen or in print in the form of a map, etc. so that a distribution state of the haze can be grasped at a glance by a user.

The distribution state determination part 4i determines whether the haze distribution obtained by the haze distribution calculation part 4g represents a predetermined distribution state. In the present embodiment, the apparatus is configured to determine whether the haze distribution shows the predetermined distribution state by an inspection history, that is stored multiple time inspection results of the haze distribution.

If the following are satisfied, it is determined that the haze is growing. (1) An n-th inspection result of a haze shows a predetermined distribution state that only at positions distant from the pattern area Sx, comparatively small hazes are distributed, whereas at positions near the pattern area Sx, hazes are not distributed. (2) In addition, an (n+1)-th inspection result of the haze shows the predetermined distribution state that only at positions distant from the pattern area Sx, comparatively large hazes are distributed, whereas at positions near the pattern area Sx, smaller hazes are distributed. Here, n is a natural number.

Figure 7:
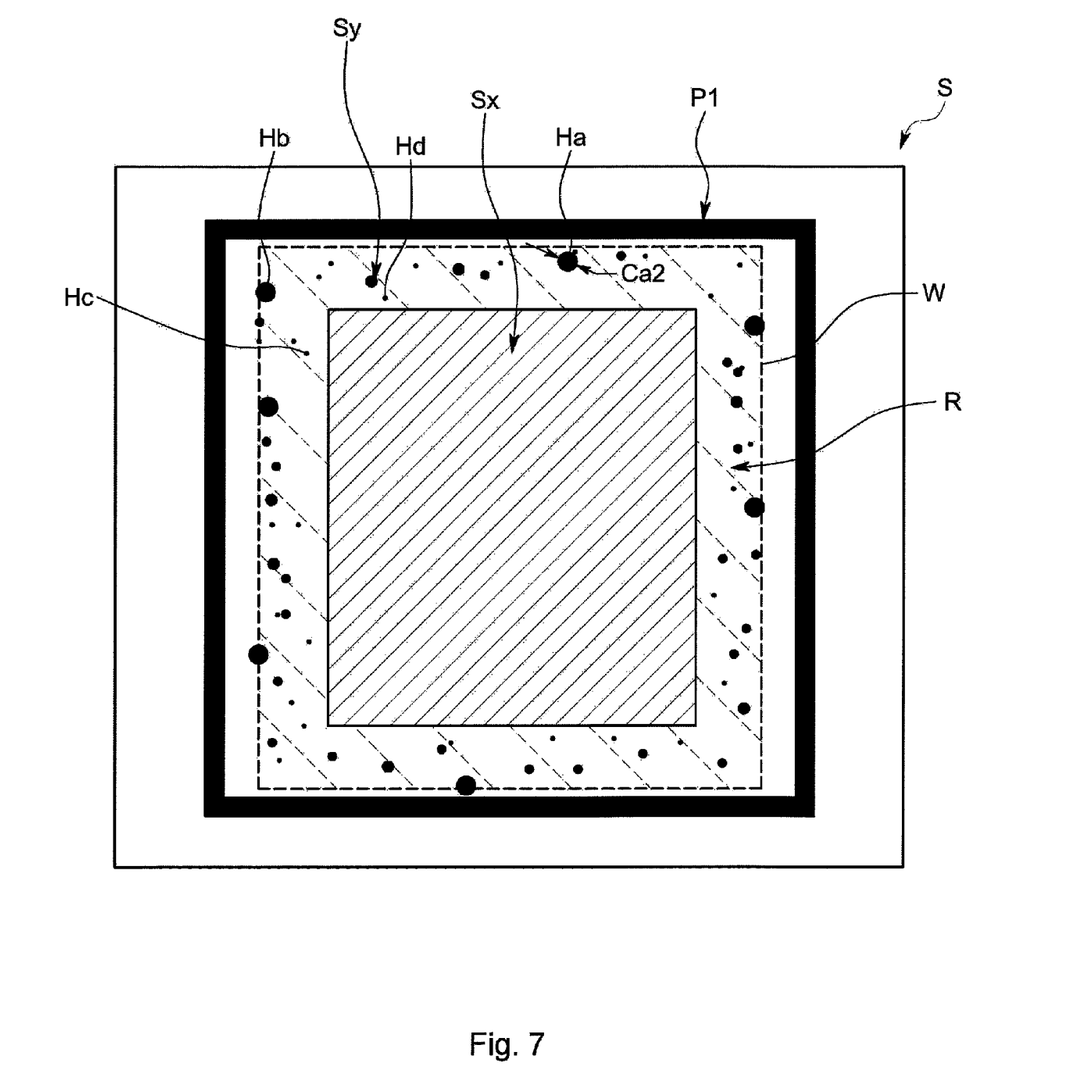
FIG. 7 is a diagram showing a state where the haze generated in a growth stage.

For example, in a case where inspection results of the haze show predetermined distribution states as follow, it is determined that the haze is growing. (1) The inspection result of the last time indicates the predetermined distribution state, as shown in FIG. 6, that only at positions distant from the pattern area Sx, comparatively small hazes Ha, Hb, etc. are distributed, whereas at positions near the pattern area Sx, hazes are not distributed. (2) The inspection result of this time period indicates from the predetermined distribution state, as shown in FIG. 7, that at positions distant from the pattern area Sx, comparatively large hazes Ha, Hb, etc. are distributed, whereas at positions near the pattern area Sx, smaller hazes Hc, Hd, etc. are distributed.

In addition, in the present embodiment, this distribution state determination part 4i is configured to, when it determines that the result is one that indicates the predetermined distribution state, outputs a report that the haze is growing.

Incidentally, it is natural that whether it shows the predetermined distribution state can be determined by, for example, from only a one time inspection result of a haze distribution, than comparing multiple time inspection results of the haze distribution among them is not necessary.

Next, an operation when haze inspection is performed using the defect inspection apparatus A configured in this way will be explained referring to the drawings.

First, as shown in FIG. 5, defect inspection is performed by sequentially scanning an area enclosed by a dashed line frame W.

When the scanned inspection lights L1 is diffracted and/or scattered by a defect on the surface Sa of the sample S or the pellicle film P2, the photodetector 32 detects this diffracted and/or scattered detection light L2 and outputs a scattered-light detection signal indicating the intensity, etc. of the detection light L2.

When the signal receive part 4a of the information processor 4 receives the scattered-light detection signal from the photodetector 32, an unillustrated storage propriety determination part provided in the information processor 4 determines whether the intensity of the detection light L2 indicated by this scattered-light detection signal exceeds a predetermined threshold. Then, when the storage propriety determination part determines that the intensity of the detection light L2 exceeds the predetermined threshold, the intensity of the light and the inspection position that is obtained by a stage address indicated by the stage address signal and the mirror angle signal are correlated with each other and stored in the storage part 4b.

Here, in the present embodiment, the storage propriety determination part is configured to read a window function—provided in the storage part 4b—showing an inside area that is the non-pattern area and in which the pellicle frame P1 is provided, namely an inspection target area R (portion hatched by dashed lines) sandwiched between the dashed-line frame W shown in FIG. 5 and the pattern area Sx and the like at the time of storing in the storage part 4b, and set an area shown by the function as the examination target area. Then it can determine whether the inspection position at which the intensity of the detection light L2 exceeds the predetermined threshold falls in an area indicated by the function and, when it is determined that the inspection position falls within the inspection target area R, perform storage with the intensity of light correlated with the inspection position.

That is, since even when an area enclosed by the dashed line frame W is scanned, the storage propriety determination part is configured not to store an inspection result when the pattern area Sx is scanned, the following haze inspection can be performed only from the inspection result when the inspection target area R is scanned, without being affected by the detection light from the pattern.

(1) Inspection by Particle Size of Haze

When an unillustrated instruction accept part accepts an instruction that inspection by the particle size of a haze be performed, the haze size calculation part 4c calculates the particle size of the haze when an area shown in FIG. 5 is scanned based on the intensity of light stored in the storage part 4b, and stores it in the calculation result storage part 4j. Then, when the particle size variation determination part 4d determines "the particle size of the haze inspected this time has become larger than the particle size of the haze inspected at the last time period and stored in the calculation result storage part 4j," it outputs a report that the haze is growing.

(2) Inspection by Inspection Clearance that is Clearance from Haze to Pattern Area Sx When an unillustrated instruction accept part accepts an instruction that inspection by the inspection clearance be performed, the clearance calculation part 4e calculates the inspection clearance when an area shown in FIG. 5 is scanned based on the inspection position on the surface Sa, FIG. 1 stored in the storage part 4b, and stores it in the calculation result storage part 4j. Then, when the clearance determination part 4f determines "the inspected clearance stored in the calculation result storage part 4j is equal to or less than the predetermined distance," it outputs a report that the haze is growing.

(3) Inspection by Haze Distribution

When an unillustrated instruction accept part accepts an instruction that inspection by a haze distribution be performed, the haze distribution calculation part 4g calculates the size of each haze in the same manner as the haze size calculation part 4c, also calculates a haze distribution when an area shown in FIG. 5 is scanned based on the inspection position of each haze, and stores it in the calculation result storage part 4j.

Then, the distribution state determination part 4i compares the inspection results of the last time period stored in the calculation result storage part 4j and the inspection of the current time period, and if it determines as follow, it outputs a report that the haze is growing. (1) The last inspection result of the haze indicates the predetermined distribution state that, as shown in FIG. 6, only at positions distant from the pattern area Sx, comparatively small hazes are distributed, whereas at positions near the pattern area Sx, the hazes are not distributed. (2) Current time period inspection result of the haze indicates the predetermined distribution state that, as shown in FIG. 7, at positions distant from the pattern area Sx comparatively large hazes are distributed, whereas at positions near the pattern area Sx, smaller hazes are distributed. Simultaneously, the haze distribution output part 4h is configured to output the haze distribution of each time on a screen.

Therefore, since according to the defect inspection apparatus A according to the present embodiment configured as described above, the inspection target area is set in the non-pattern area Sy, a problem of erroneous detection by the effect of the detection light from the pattern is not produced, and the inspection time can be shortened compared with a case of inspecting the entire surface like a conventional defect inspection apparatus. Further, since even when the sensitivity is improved in order to inspect a haze in the developmental stage having a small particle size, only the non-pattern area Sy needs to be inspected, the effect of a lowered throughput by improved sensitivity becomes small compared with the case of inspecting the entire surface.

In addition, since only by obtaining an inspection result that there is no haze in the non-pattern area Sy, it can be determined that there is no generation of a haze also in the pattern area Sx, thereby shortening of the inspection time can be suitably attained. In addition, if the inspections of (1)-(3) are combined, it will contribute to improvement of correctness of the determination. Then when it is determined that a haze exists or is growing in the non-pattern area Sy, if a measure, such as cleaning or exchange of the pellicle P or halt of its use, is taken at that stage, it becomes possible to prevent the production yield of the semiconductor device from being lowered by the haze condition.

That is, the present invention can provide an excellent defect inspection apparatus A that is simple yet can detect a haze with high precision and at a high speed, so as to be able to prevent the production yield of the semiconductor device from being lowered by a haze problem.

Incidentally, there are several causative agents to create a haze. However, in any case, similarly a gas is converted into a particle, which develops on the surface Sa of the reticle/mask and the surface Sa (a surface on the side of reticle/mask) of the pellicle film P2. Difference of the causative agent only appears in a point that the haze can be detected when the particle is smaller or the haze can be detected when it has become larger because of a scattering characteristic of that material. Therefore, the defect inspection apparatus A can inspect even a haze whose causative agent is not clear without carrying out a special contrivance depending on the causative agent. Consequently, what is necessary is just to give a contrivance in terms of software, such as inspecting the non-pattern area Sy, as an improvement to the conventional defect inspection apparatus, and thereby not bringing about an increase in hardware of the apparatus.

In addition, the present invention is not restricted to the above embodiment. For example, a configuration of the pellicle P is not restricted to the present embodiment.

Figure 8:
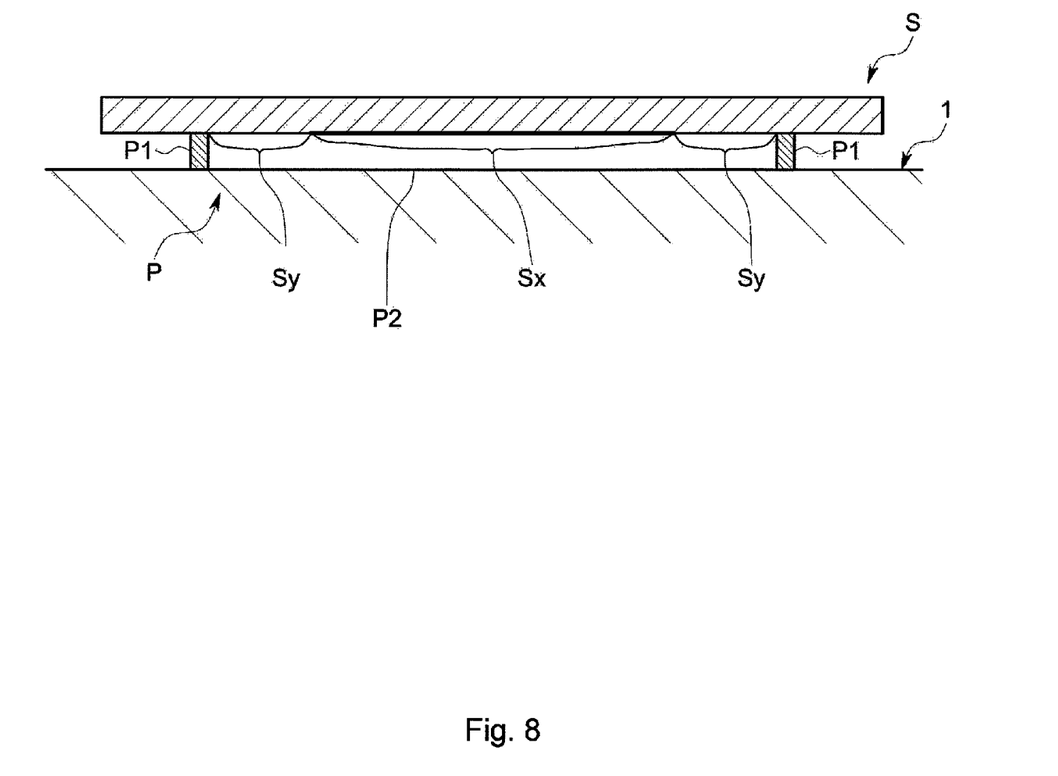
FIG. 8 is a diagram showing a mounting mode of the sample and the pellicle.

In addition, in the present embodiment, although explanation was given on the inspection of the surface Sa of the sample S, inspection of the back surface of the sample and of the surface of the pellicle film may also be performed. As shown in FIG. 8, it is also possible to perform inspection by placing the pellicle P and the sample S on the stage 1 in this order from the bottom.

In addition, in the present embodiment, although in order to simplify a scanning operation, it was specified to scan the whole surface, only the non-pattern area Sy as the inspection target area may be scanned. This is because if such a configuration is adopted, the determination by the storage propriety determination part described above becomes unnecessary in storing the intensity of light and the inspection position in the storage part 4b.

Moreover, a configuration in which the stage 1 is an X-Y stage and the light detection system 3 are mounted on a Z-stage may be adopted.

Furthermore, a configuration in which the stage 1 is fixed and the light detection system 3 are mounted on the X-, Y-, and Z-stages may be adopted.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A defect inspection apparatus, comprising:
   a light source for illuminating inspection light on a sample with an inspection target plane that has a pattern area in which a pattern is formed and a non-pattern area in which a pattern is not formed, and has a frame member for supporting a protective coat for preventing an adhesion of foreign matters on the pattern area and the non-pattern area;
   means for defining an inspection target area on the inspection target plane;
   a light scanning part for scanning the inspection light on the inspection target plane; and
   a photodetector that, when the light scanning part scans the inspection light on the inspection target plane, detects light diffracted and/or scattered by the inspection target plane and provides output signals;
   wherein the inspection target area is set in the non-pattern area for defining the output signals to be processed to monitor a condition of the sample.

2. The defect inspection apparatus according to claim 1, comprising:
- a haze size calculation part for calculating a particle size of a haze condition based on the detection light detected by the photodetector when the inspection target area is scanned; and
- a particle size variation determination part for determining whether the particle size of the haze obtained by the haze size calculation part has become larger in comparison with a previous inspection result of the same inspection position.

3. The defect inspection apparatus according to claim 1, further comprising:
- a clearance calculation part for calculating a clearance distance from the haze to the pattern area of the sample based on the detection light detected by the photodetector when the inspection target area is scanned.

4. The defect inspection apparatus according to claim 1, comprising:
- a haze distribution calculation part for calculating a distribution of a haze in the non-pattern area based on the detection light detected by the photodetector when the inspection target area is scanned; and
- a haze distribution output part for outputting the haze distribution obtained by the haze distribution calculation part.

5. The defect inspection apparatus according to claim 1, comprising:
- a haze distribution calculation part for calculating a distribution of a haze in the non-pattern area based on the detection light detected by the photodetector when the inspection target area is scanned; and
- a distribution state determination part for determining whether the haze distribution obtained by the haze distribution calculation part is one that shows a predetermined distribution state.

6. A defect inspection apparatus, comprising:
- a light source for illuminating inspection light on an inspection target plane that has a pattern area in which a pattern is formed and a non-pattern area in which a pattern is not formed, and has a frame member for supporting a protective coat for preventing an adhesion of foreign matters on the pattern area being provided in the non-pattern area;
- a light scanning part for scanning the inspection light on the inspection target plane; and
- a photodetector that, when the light scanning part scans the inspection light on the inspection target plane, detects light diffracted and/or scattered by the inspection target plane;
- wherein the inspection target area is set in the non-pattern area.

7. The defect inspection apparatus according to claim 6, comprising:
- a haze size calculation part for calculating a particle size of a haze based on the detection light detected by the photodetector when the inspection target area is scanned; and
- a particle size variation determination part for determining whether the particle size of the haze obtained by the haze size calculation part has become large in comparison with the last inspection result.

8. The defect inspection apparatus according to claim 6, further comprising
- a clearance calculation part for calculating a clearance from the haze to the pattern area based on the detection light detected by the photodetector when the inspection target area is scanned.

9. The defect inspection apparatus according to claim 6, comprising:
- a haze distribution calculation part for calculating a distribution of a haze in the non-pattern area based on the detection light detected by the photodetector when the inspection target area is scanned; and
- a haze distribution output part for outputting the haze distribution obtained by the haze distribution calculation part.

10. The defect inspection apparatus according to claim 6, comprising:
- a haze distribution calculation part for calculating a distribution of a haze in the non-pattern area based on the detection light detected by the photodetector when the inspection target area is scanned; and
- a distribution state determination part for determining whether the haze distribution obtained by the haze distribution calculation part is one that shows a predetermined distribution state.

* * * * *